(12) United States Patent
Hopman et al.

(10) Patent No.: US 9,320,839 B2
(45) Date of Patent: Apr. 26, 2016

(54) MULTI-FUNCTION HAND PUMP FOR MEDICAL USE

(71) Applicant: The Seaberg Company, Inc., Wilsonville, OR (US)

(72) Inventors: Lance D. Hopman, Tigard, OR (US); Lane M. Johnson, Chandler, AZ (US); Eric E. Batdorf, Oregon City, OR (US)

(73) Assignee: The Seaberg Company, Inc., Wilsonville, OR (US)

( * ) Notice: Subject to any disclaimer, the term of this patent is extended or adjusted under 35 U.S.C. 154(b) by 205 days.

(21) Appl. No.: 14/108,112

(22) Filed: Dec. 16, 2013

(65) Prior Publication Data
US 2014/0171889 A1 Jun. 19, 2014

Related U.S. Application Data

(60) Provisional application No. 61/737,745, filed on Dec. 15, 2012.

(51) Int. Cl.
*A61M 1/00* (2006.01)
*A61B 17/135* (2006.01)

(52) U.S. Cl.
CPC ........... *A61M 1/0011* (2013.01); *A61M 1/0019* (2013.01); *A61M 1/0072* (2014.02); *A61M 1/0076* (2013.01); *A61B 17/135* (2013.01); *A61B 2217/005* (2013.01); *A61M 2205/075* (2013.01)

(58) Field of Classification Search
CPC ............ A61M 1/0011; A61M 1/0072; A61M 2205/075; A61M 1/0019
See application file for complete search history.

(56) References Cited

U.S. PATENT DOCUMENTS

| 3,312,221 | A |   | 4/1967  | Overment |
|-----------|---|---|---------|----------|
| 4,392,858 | A | * | 7/1983  | George ............... A61M 1/0011 604/126 |
| 4,551,141 | A |   | 11/1985 | McNeil |
| 4,828,546 | A | * | 5/1989  | McNeil ............... A61M 1/0011 604/133 |
| 5,009,635 | A | * | 4/1991  | Scarberry .......... A61M 1/0011 604/27 |
| 5,062,835 | A | * | 11/1991 | Maitz .................. A61M 1/0023 604/153 |
| 5,346,477 | A |   | 9/1994  | Edwards et al. |
| 7,909,805 | B2 |  | 3/2011  | Weston |
| 2006/0079853 | A1 | | 4/2006 | Christensen et al. |

(Continued)

FOREIGN PATENT DOCUMENTS

WO     2005052366 A2    6/2005

OTHER PUBLICATIONS

EM Innovations, Suction-Easy Manual Emergency Suction Unit, web pages, found at http://www.eminnovations.com/suctioneasy.htm on Dec. 6, 2013.

(Continued)

*Primary Examiner* — Susan Su
(74) *Attorney, Agent, or Firm* — Chernoff, Vilhauer, McClung & Stenzel, LLP

(57) ABSTRACT

A small manually operable pump which may be of the squeeze-bulb type, arranged to reduce fluid pressure and receive a fluid at a first end and to discharge a flow from an opposite end, and provided with a connector at each end so that it can be connected to various articles of emergency medical equipment to provide increased pressure or suction as required. A collection bag is arranged to use both the suction and the pressurized flow of the pump to suck materials from a wound or a patient's airway into the collection bag.

6 Claims, 6 Drawing Sheets

(56) References Cited

U.S. PATENT DOCUMENTS

| | | | |
|---|---|---|---|
| 2007/0027433 A1 | 2/2007 | Garcia et al. | |
| 2007/0197969 A1 | 8/2007 | Hillborg et al. | |
| 2009/0306609 A1 | 12/2009 | Blott et al. | |
| 2010/0305549 A1* | 12/2010 | Miller | A61M 1/0088 604/543 |
| 2013/0226114 A1* | 8/2013 | Massi | A61M 1/0023 604/318 |
| 2014/0121613 A1* | 5/2014 | Baratian | A61J 1/10 604/318 |

OTHER PUBLICATIONS

Conterra Inc., "The Squid" Telescoping Suction Device, found at http://ww.conterr-inc.com/index.php?dispatch+products.view&product_id=189 on Dec. 6, 2013.

Bard Access Systems, Inc, "Aspira Peritoneal Drainage System," found at http:..www.bardaccess.com/drainage-aspira-peritoneal-bv.php on Dec. 6, 2013.

Bard Access Systems, Inc, "AirGuard Valved Introducer," Salt Lake City, Utah.

* cited by examiner

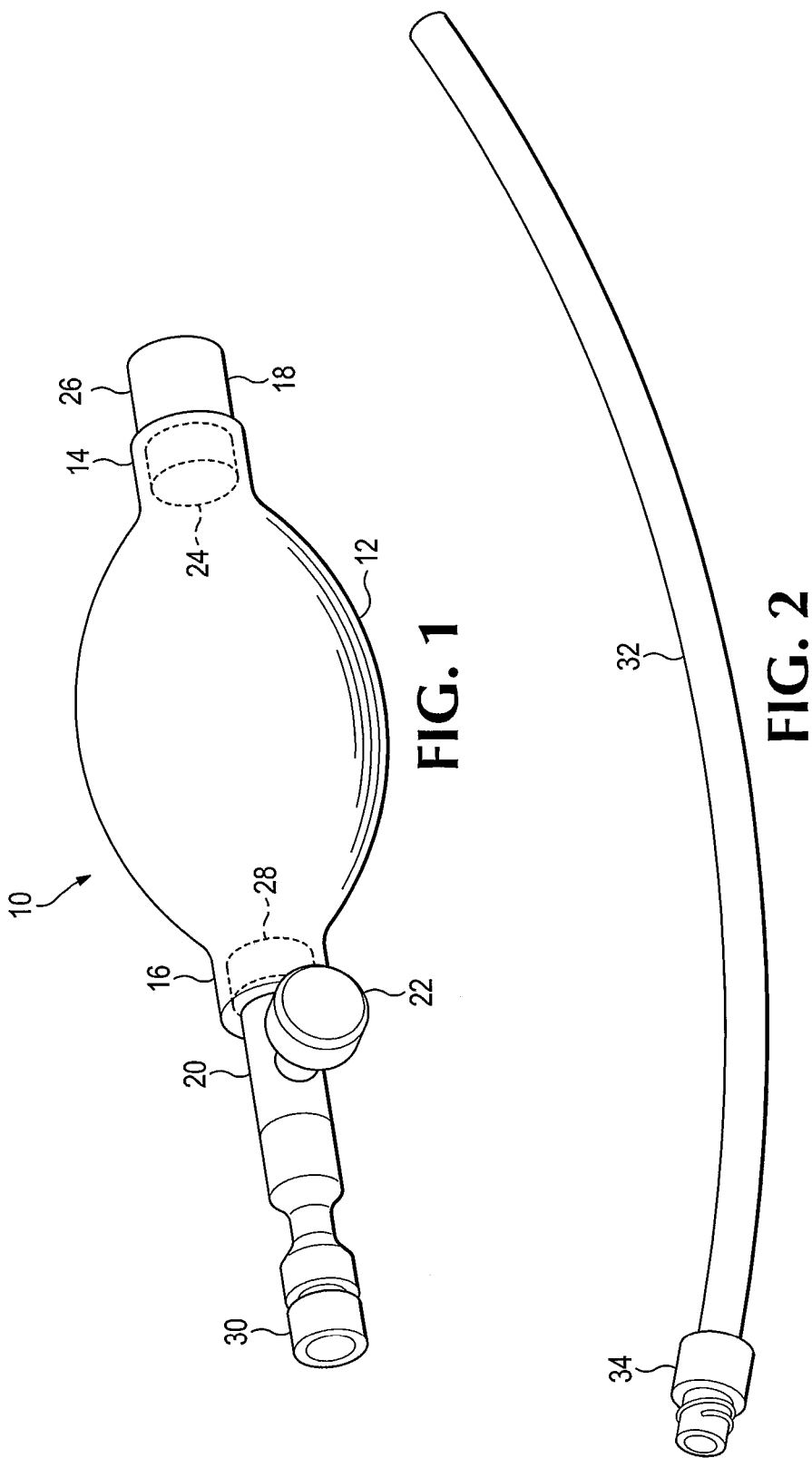

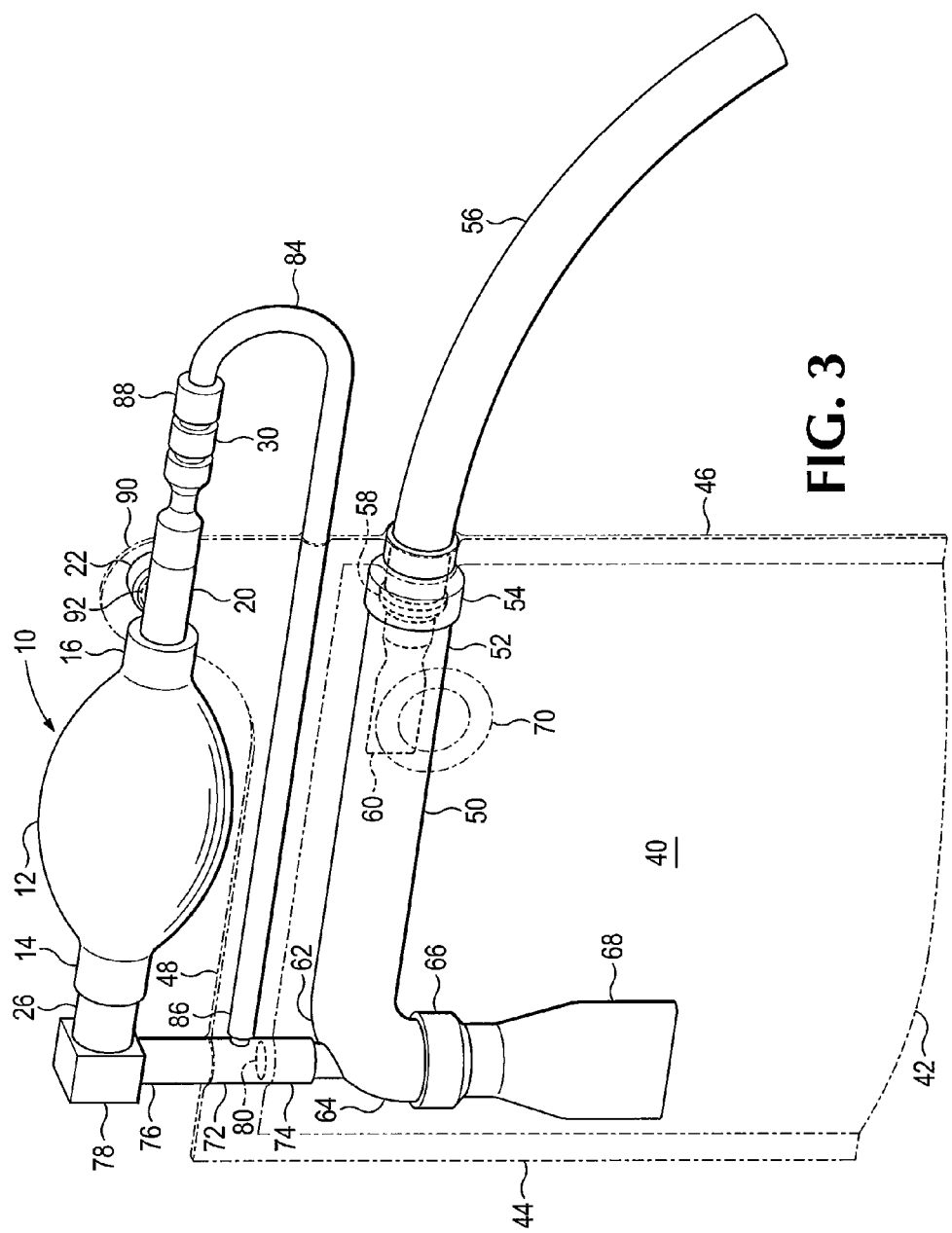

MULTI-FUNCTION HAND PUMP FOR MEDICAL USE

CROSS-REFERENCE TO RELATED APPLICATIONS

The present application claims the benefit of the filing date of U.S. provisional patent application No. 61/737,745, filed Dec. 15, 2012.

BACKGROUND OF THE INVENTION

The present disclosure relates to devices capable of carrying out multiple functions in connection with emergency medical care, as provided in the field by military medical personnel and by other emergency medical care providers. The devices disclosed herein are intended to complement the equipment typically carried by a combat medic, by providing a single pump useful for suction of fluids, as from wounds or in connection with decompression of tension pneumothorax, or in clearing airways, and for inflation of devices such as splints, balloon catheters, and inflatable pressure-application elements of tourniquets.

Emergency medical care providers, especially in military situations, at athletic events, for example, must be prepared to deal with various types of injuries and must have the best possible assortment of equipment available in a conveniently carried package such as a small medical bag or backpack.

Some emergency devices, such as inflatable splints, or bladders utilized to apply pressure to stop bleeding, can be carried in a compact configuration, but require inflation at the time of use.

Some types of injuries that may be treated by emergency personnel indicate application of suction to remove fluids such as blood, including blood clots, from wounds to a person's torso, or to clear airways for breathing.

It is desired, then, to provide a device which can serve multiple purposes, including inflation and suction for use in connection with various elements of emergency medical equipment likely to be carried by emergency medical service providers.

SUMMARY OF THE INVENTION

As one aspect of the disclosure herein, a manually operated pump is provided that can be utilized both to provide increased air pressure to inflate a medical device and to provide reduced pressure, or suction, for use in removing fluids from a patient's wounds an airway or other bodily openings.

In a device embodying one aspect of the disclosure herein, a manually operable squeeze bulb pump includes connectors to which suction tubes or inflation tubes can be attached, so that the pump can be used to move undesired fluids away from a patient or to inflate a splint or a bladder that might be used to apply pressure to stop bleeding.

As one aspect of the disclosure herein, such a multi-purpose hand pump may be connected for use in combination with a vacuum chamber, a suction tube, and a collection bag for use in collecting fluids, as from an open abdominal or thoracic wound.

As another aspect of the invention disclosure herein, such a multi-purpose hand pump may be connected for use in combination with a Venturi eductor, a suction tube, and a collection bag.

As yet a further aspect of the invention disclosure herein, such a multi-purpose hand pump may be connected so as to pump liquids and entrained semi-solids and solid materials through the pump and into a collection bag.

The foregoing and other features of the present disclosure will be more readily understood upon consideration of the following detailed description of various embodiments, taken in conjunction with the accompanying drawings.

BRIEF DESCRIPTION OF THE SEVERAL DRAWINGS

FIG. 1 is an isometric view of a multi-function hand pump according to an embodiment of an aspect of the invention disclosed herein.

FIG. 2 is an isometric view of a suction tube adapted for use together with the hand pump shown in FIG. 1.

FIG. 3 is a partially cutaway isometric view of a multi-function hand pump such as that shown in FIG. 1, in use together with a vacuum chamber and a collection bag in accordance with another aspect of the invention disclosed.

DETAILED DESCRIPTION OF PREFERRED EMBODIMENTS

Figure 4:
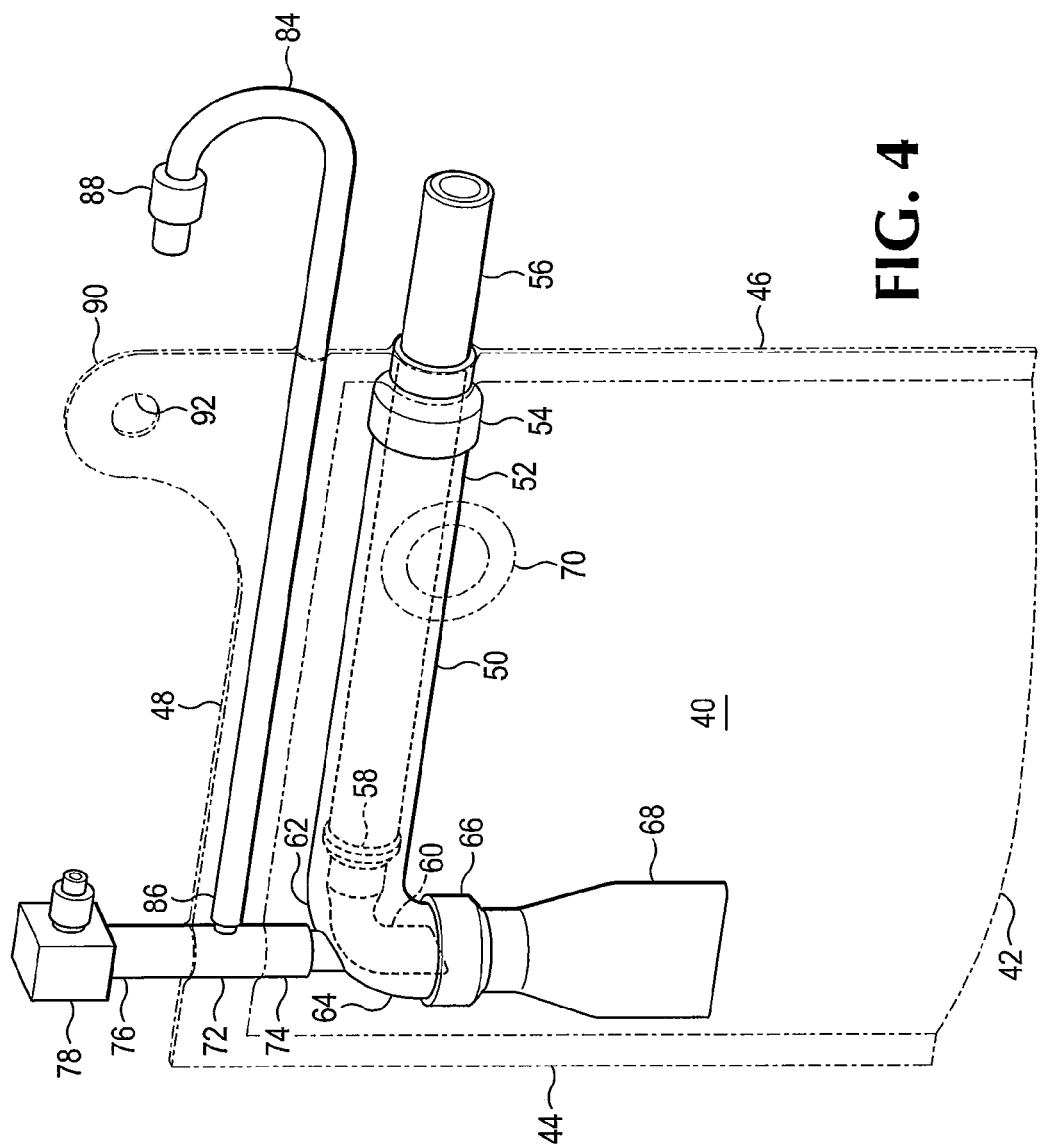
FIG. 4 is a view similar to that of FIG. 3, showing the collector bag without the hand pump, and showing an evacuation tube in a stowed position.

Referring now to the drawings which form a part of the disclosure herein, a multi-purpose hand pump 10 shown in FIG. 1 includes a hollow ovoid squeeze bulb 12 having a pair of openings at its opposite ends 14 and 16. The squeeze bulb 12 may be manufactured of a resilient and elastically flexible material such as a synthetic rubber or silicone material. For example, PVC is an acceptable material. Preferably, the squeeze bulb 12 may be able to exert a vacuum in the vicinity of 100 MM Hg when squeezed and then released.

A short inflow conduit 18 is connected to and in communication with the opening at the inflow end 14 of the squeeze bulb 12, and an outflow conduit 20 is connected to and in communication with the opening at the outflow end 16 of the squeeze bulb 12. A manually controlled bleed valve 22 is mounted in the outflow conduit 20, where it can be opened to release gas and thus relieve pressure from the outflow conduit and any system connected to the outflow conduit 20.

A check valve 24 and suitable connector 26, such as a Luer connector, are mounted at an inner end of the inflow conduit 18, with the check valve 24 oriented to allow fluid to flow into the squeeze bulb 12 through the inflow conduit 18, but to prevent fluid from flowing out from the squeeze bulb 12 through the inflow conduit 18.

A check valve 28 may be located at an inner end of the outflow conduit 20, with the check valve 28 oriented to allow fluid to flow out from the squeeze bulb 12 through the outflow conduit 20, but to prevent fluid from flowing into the squeeze bulb 12 through the outflow conduit 20. A connector 30, such as a Luer connector 30 or equivalent, may be mounted at an outer end of the outflow conduit 20.

As shown in FIG. 2, a suction tube 32 of a standard size may be of a suitable rubber or plastics material with a wall thickness sufficient to withstand vacuum. The suction tube 32 may have a length suitable for the intended use, and may include a Luer connector 34 at one end to permit the suction tube 32 to be connected to one of the connectors 26 and 30 of the multi-purpose hand pump 10. The suction tube 32 may thus be utilized as a suction tube when connected to the inflow conduit 18.

As shown in FIGS. 3 and 4, in a collection system 38 the multipurpose hand pump 10 may be used in combination with a collection bag 40, which may be manufactured of a suitably strong yet thin and flexible plastics membrane folded along a bottom end 42 and with the resulting two parallel layers of the membrane sealingly connected to each other along a pair of sides margins 44 and 46 and a top margin 48.

Within an upper part of the collection bag 40 is a structure defining a vacuum chamber 50, which may be generally tubular and may be made of a generally rigid plastics material. A first end 52 may extend through and be included and sealed in the side margin 46 of the collection bag 40. The evacuation tube 56 may be of an accepted standard diameter and wall thickness. A slip fitting 54 or gland at the first end 52 may have an externally open receptacle in which an evacuation tube 56 is slidably disposed. A connector 58 on the inner end of the evacuation tube 56 is thus located inside the generally tubular vacuum chamber 50 and includes a collar that is larger than the opening through the slip fitting 54, and thus prevents the tube 56 from being over-extended. A one-way valve 60 such as a flutter valve is sealingly connected with the inner end connector 58 to allow fluid flow into the vacuum chamber 50 from the evacuation tube 56, but to prevent fluid flow in the opposite direction. Such a one-way valve 60 may be simply a length of flat tubing of flexible material such as that of the collection bag 40 that can be pressed shut by external air pressure, yet can open easily to permit material to pass through in the desired direction from the connector 58.

An opposite second end 62 of the vacuum chamber 50 may include an elbow 64 with an exhaust or bottom end 66 directed downwardly into the interior of the bag 40, and with a flutter valve 68, or another suitable one-way valve, connected to the downwardly-directed bottom end 66 of the elbow 64. An exhaust port or vent 70 may be provided in an upper part of a wall of the collection bag 40. Fluid which may include a mixture of liquid and gas may then enter into the collection bag 40 through the evacuation tube 56, the flutter valve 60, and vacuum chamber 50, exiting from the vacuum chamber 50 through the elbow 64 and the flutter valve 68. Liquid and entrained solids may then accumulate near the bottom 42 of the collection bag 40 while gas exits through the vent 70.

A two-way conduit 72 extends into the collection bag 40 near its upper margin, as by being sealed into the top margin 48 portion of the collection bag 40. A bottom or inner end 74 of the two-way conduit 72 is connected to the elbow 64, and the interior of the conduit 72 communicates with the interior of the elbow 64. The Luer connector 26 connects the inflow conduit 18 at the inflow end 14 of the multi-purpose hand pump 10 to the connector 78 at the upper end 76 of the conduit 72. An appropriate connector such as a compatible 90 degree angled quick-disconnect connector 78 may be associated with the upper or outer end of the conduit 72. An upper or outer end 76 of the conduit 72 is connected to the Luer connector 26 and the associated inflow check valve 24 of the inflow conduit 18 at the inflow end 14 of the multi-purpose hand pump 10. A screen 80 may be installed in the bottom or inner end 74 of the conduit 72, to prevent solids from entering into the conduit 72 from the vacuum chamber 50.

The multi-purpose hand pump 12 may be used, then, to create a suction by reducing pressure within the vacuum chamber 50, so that fluids can be drawn into the vacuum chamber 50 through the evacuation tube 56. Material can then flow downward under the influence of gravity through the elbow 64 and the flutter valve 68, into the interior of the collection bag 40.

Flow into the collection bag 40 of liquid and solid materials entrained in gas drawn into the vacuum chamber 50 is enhanced in the system shown in FIGS. 3 and 4 by the use of an overpressure conduit 84. The overpressure conduit 84 may extend along the top margin 48 of the collection bag 40 and may be held in place and sealed from the surrounding ambient air by being sealed within the margin portion 48 at the top of the collection bag 40. A discharge end 86 of the overpressure conduit 84 and extends to and is connected in communication with the two-way conduit 72 above the screen 80. The opposite, outer, or infeed end of the overpressure conduit 84 extends from the top margin 48 and has a fitting 88 that is compatible with and is connected with the Luer fitting 30 at the outflow end 16 of the squeeze bulb 12.

To help keep the multipurpose hand pump 10 aligned with the 90° connector 78 and to avoid unnecessary strain on the overpressure conduit 84, an ear 90 may be provided at the top of the collection bag 40. The ear 90 defines an opening 92 through which the operating knob of the bleed and check valve 22 may be inserted, to keep the multi-purpose hand pump 10 oriented closely along the top margin 48 of the collection bag 40.

With the overpressure conduit 84 connected with the outflow Luer connector 30 of the pump 10, when the squeeze bulb 12 is squeezed gas is driven at an increased pressure through the overpressure conduit 84 and from its discharge end 86 into the two-way conduit 72, pushing material from the vacuum chamber 50 and elbow 64 down through the bottom end 66 of the elbow 64 and through the flutter valve 68 into the interior of the collection bag 40. As explained above, denser liquid and solid material can descend to the bottom of the collection bag 40 while gas can escape through the vent 70. It will be understood, then, that repeated squeezing and releasing of the squeeze bulb 12 will result in fluids being drawn effectively through the evacuation tube 56 in a pulsating flow into the collection bag 40.

As shown in FIG. 4, the evacuation tube 56 may be housed at least partially within the vacuum chamber 50 by sliding it through the slip fitting 54 at the outer end of the vacuum chamber 50. The flutter valve 60 is thus pushed toward or into the elbow 64 with the evacuation tube.

Figure 5:
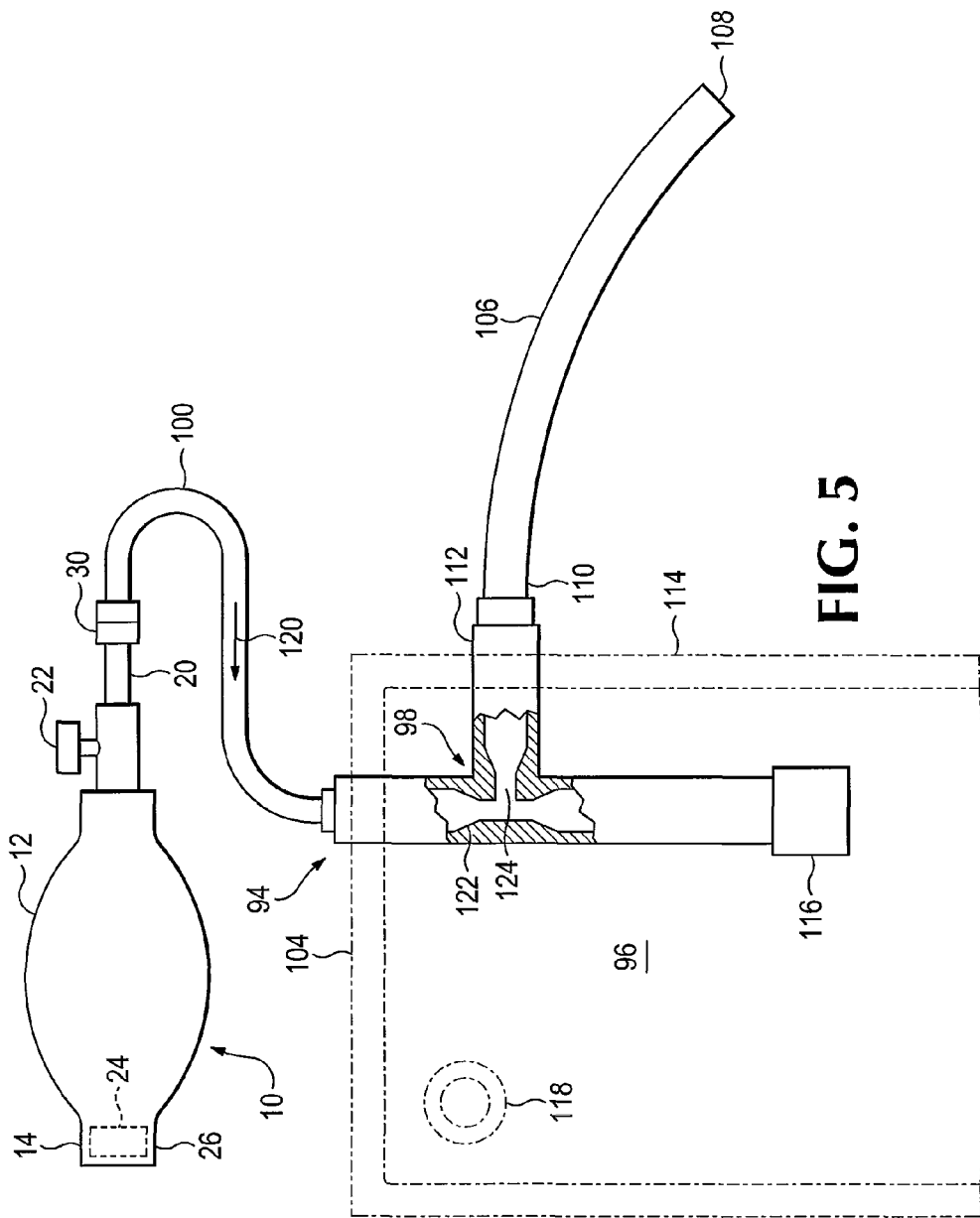
FIG. 5 is a partially cutaway, partially diagrammatic view showing a multi-function hand pump such as that shown in FIG. 1, in use together with a Venturi eductor arranged to collect material in a collection bag.

Referring next to FIG. 5, the multi-purpose hand pump 10 is shown in use in connection with an evacuator system 94 including a collection bag 96 generally similar to the collection bag 40, but with a Venturi eductor 98 instead of the vacuum chamber 50 and its associated elements that are present in the collection bag 40. An overpressure conduit 100 has a discharge end 102 that may be sealed into a top margin 104 of the collection bag 96 and which is connected to the Venturi eductor 98 to conduct a flow of air into the Venturi eductor 98. An evacuation tube 106 has an open, outer or suction end 108 and an inner, discharge end 110 connected with a connector 112 that may be sealed into a side margin 114 of the collection bag 96, and which leads into the suction side of the Venturi eductor 98. An exhaust, or discharge, fitting 116 from the Venturi eductor nozzle preferably includes a one-way valve and allows all that has passed through the Venturi eductor to flow into the interior of the collection bag 96, where, as with the materials discharged from the vacuum chamber 50 described above, the denser materials can fall to the bottom of the collection bag 96 while gas is able to escape from the collection bag 96 through a vent 118 and thus does not accumulate and increase pressure with the collection bag 96.

Squeezing the squeeze bulb 12 of the multi-purpose hand pump 10 causes a flow of air in the direction indicated by the arrow 120 through the overpressure conduit 100, into the nozzle 122 of the Venturi eductor 98, which causes a reduced pressure just beyond the choke of the nozzle 122, where a suction port 124 admits fluids carried through the evacuation tube 106 and the suction tube connector 112 into the Venturi nozzle, and the combined flow of air from the hand pump 10 and flow from the evacuation tube 106 is exhausted through the exhaust opening 116 into the collection bag.

Figure 6:
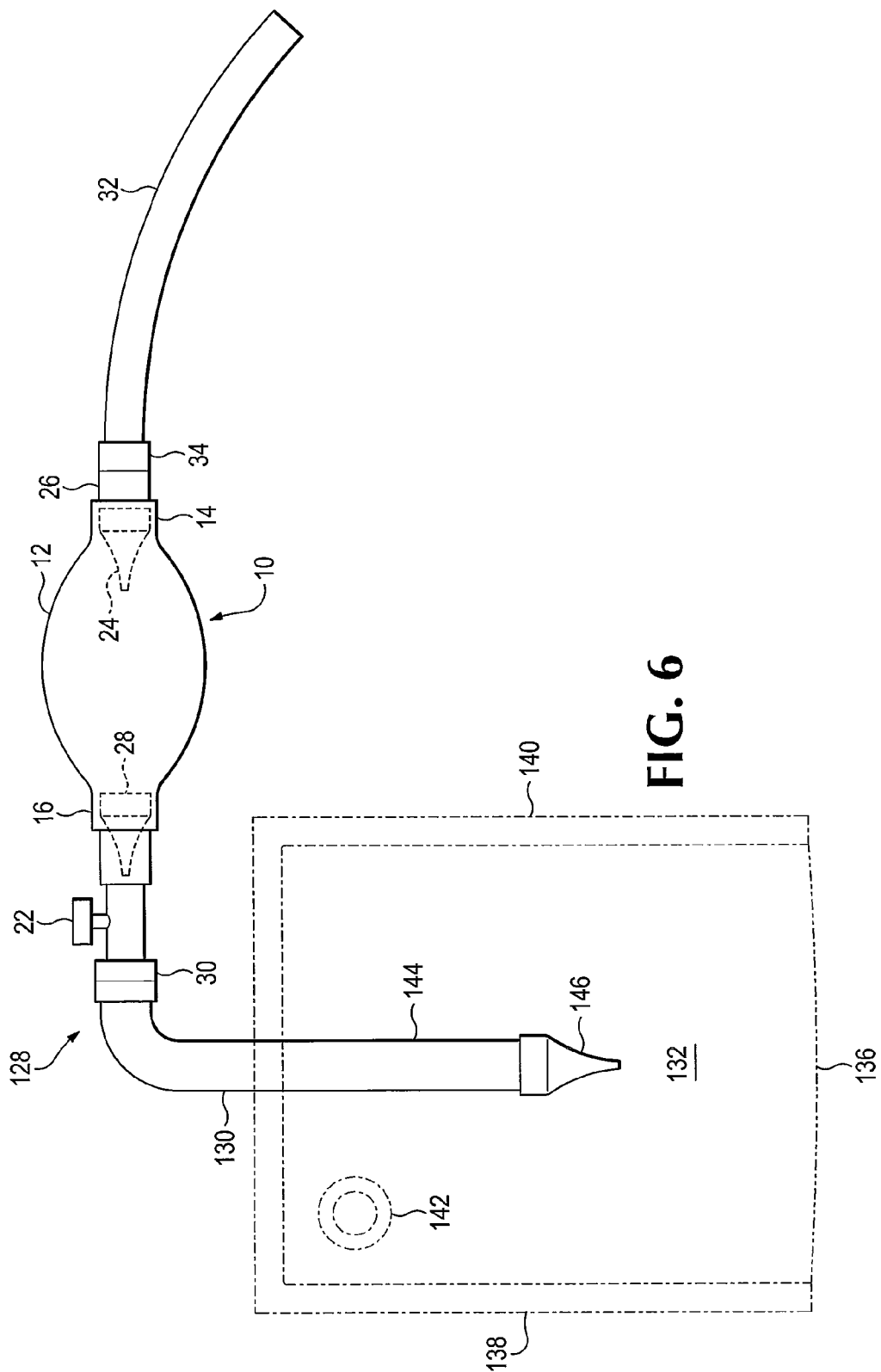
FIG. 6 is a view showing a multi-function hand pump such as that shown in FIG. 1, in use together with a collection bag to collect fluid and entrained solids aspirated from a patient.

Yet another related system 128 is shown in FIG. 6, where a suction tube such as the suction tube 32 is connected to the inflow connector 26 of the multi-purpose hand pump 10. An overpressure conduit 130 is connected to the outflow connector 30 and extends through and is preferably sealed to an upper margin 134 of the collection bag 132.

Like the collection bags 40 and 96, the collection bag 132 may have a folded bottom 136 and be of flexible plastic film material sealed along its side margins 138 and 140, and may include a vent 142 similar to the vent 70 and the vent 118. Within the collection bag 132, at a bottom, or discharge, end 144 of the overpressure conduit 130 there may preferably be a one-way valve such as a flutter valve 146 in order to admit material brought into the squeeze bulb 12 and then forced on out of the squeeze bulb 12 and through the overpressure conduit 130 into the interior of the collection bag 132 during operation of the hand pump 10. As discussed above, liquid and any entrained semi-solid or solid materials are collected in the bottom of the collection bag 132 while gas can be exhausted from the collection bag 132 through the vent 142. As shown schematically in FIG. 6, the check valves 24 and 28 in the multi-purpose hand pump 10 may be flutter valves or another type of valve designed to permit passage of particles of semi-solid or solid material yet be able to close effectively to ensure fluid passage in a single direction through the system.

Figure 7:
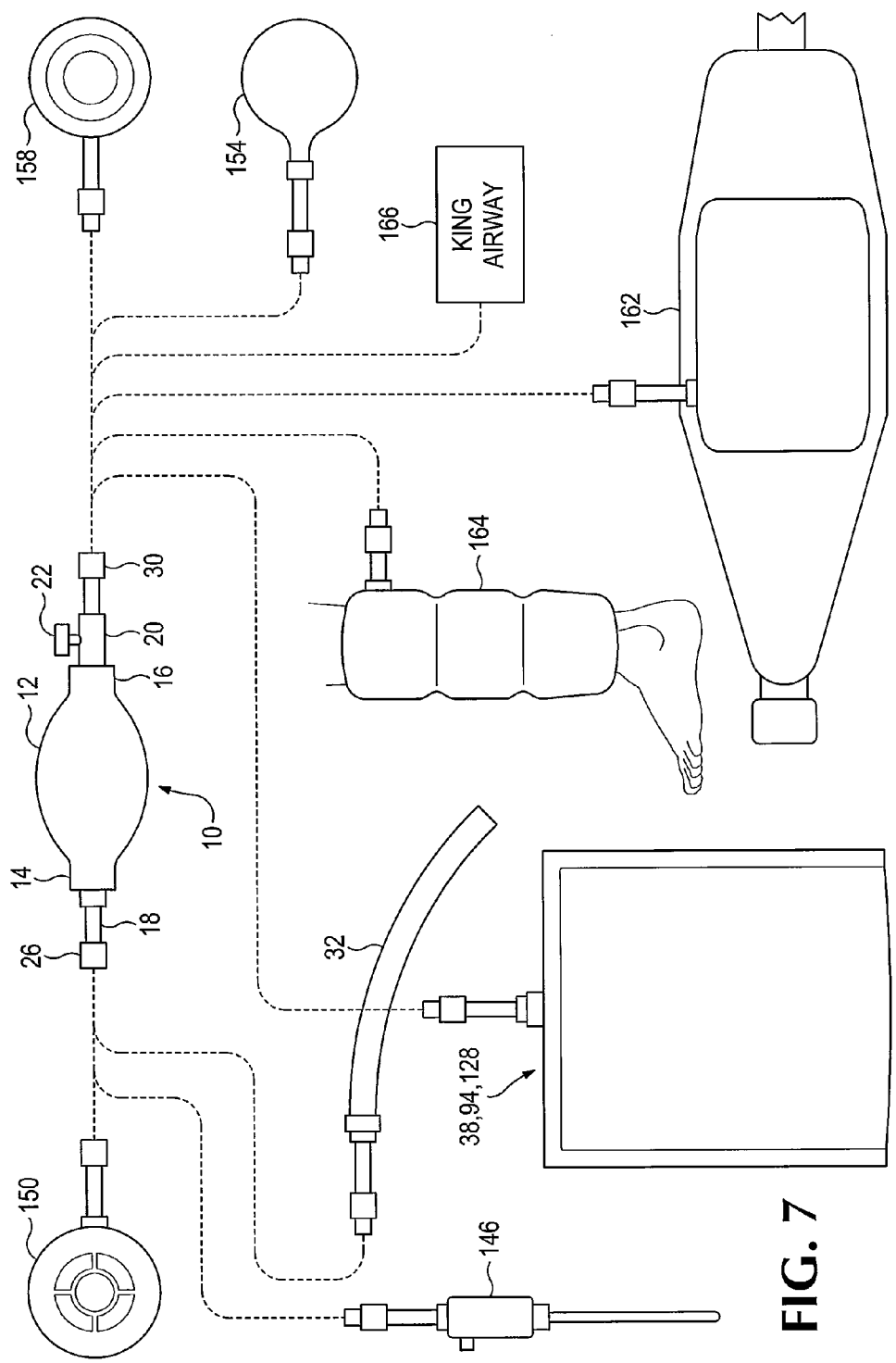
FIG. 7 is a schematic view showing applicability of the multi-purpose hand pump disclosed herein together with various items of emergency medical equipment.

As shown in FIG. 7, a single multi-purpose hand pump 10 included in an equipment bag of in an emergency medical care provider such as a military medical corpsman can be utilized effectively together with and to activate many of the medical devices carried in such an emergency medical care equipment bag. For example, the collection systems 38, 94, and 128, shown in FIGS. 3, 4, 5, and 6 and described above can be used to remove fluids from and clear a patient's airway and to collect fluids drained from the airway or from an open abdominal or thoracic wound. As another use of the pump 10, a suitable conduit may be connected between the inflow Luer connector 26 and a decompression needle device 146 such as the safety needle disclosed in pending U.S. patent application Ser. No. 3/896,026, published as U.S. patent publication document no. U.S. 2013/0310750, or may be connected to evacuate a chest tube or to a chest seal bandage 150 equipped with a compatible suction conduit and incorporating a one-way valve to apply suction to relieve a tension pneumothorax.

The pump 10 and a suitable conduit able to contain an increased pressure can be used to inflate a bladder 154 to be held against a patient by a strap system to provide pressure to stop arterial flow of blood to a hemorrhaging deep injury, for example. Such a bladder is shown, for example, in U.S. patent publication document no. U.S. 2010/0179586. Pressure can also be provided by the multi-purpose hand pump 10 to inflate a pressure concentrating device 158 useful with a truncal tourniquet such as is described in pending U.S. patent application Ser. No. 13/715,998, published as U.S. patent publication document no. U.S. 2013-0110019 A1, to stop or control hemorrhaging. Such a pump can also be used to inflate a bladder contained in a belt-like device in a pelvic sling and junctional tourniquet 162 disclosed in that same published application, or to inflate an inflatable splint 164 or a supraglottic airway such as a King airway 166.

The terms and expressions that have been employed in the foregoing specification are used therein as terms of description and not of limitation, and there is no intention in the use of such terms and expressions of excluding equivalents of the features shown and described or portions thereof, it being recognized that the scope of the invention is defined and limited only by the claims which follow.

What is claimed is:

1. A combination including a multi-function hand pump and a collection bag, the combination being arranged to collect a flow of a fluid and deliver it into the collection bag, the combination comprising:
   (a) a resilient, hollow, elastic squeeze bulb having a pair of openings;
   (b) a check valve associated with a first one of the pair of openings, arranged to allow flow of a fluid into the squeeze bulb and to prevent outward flow of fluid from the squeeze bulb;
   (c) a check valve associated with a second one of the pair of openings, arranged to allow flow of a fluid out from the squeeze bulb and to prevent inward flow of fluid into the squeeze bulb;
   (d) a respective connector associated with each one of the pair of openings, each connector communicating through the respective one of the pair of openings with an interior of the squeeze bulb;
   (e) structure defining a vacuum chamber having an outlet opening and a one-way discharge valve at the outlet opening, the outlet opening being located and arranged to allow passage of material from the vacuum chamber into an interior of the collection bag;
   (f) a two way conduit communicating between an interior of the vacuum chamber and the connector associated with the first one of the pair of openings of squeeze bulb of the hand pump;
   (g) an overpressure conduit communicating between the connector associated with the second one of the pair of openings of the squeeze bulb of the hand pump and the interior of the vacuum chamber;
   (h) a suction tube having a first end connected with and communicating with the interior of the vacuum chamber and having a second end open so as to receive and conduct a flow of fluid into the vacuum chamber; and
   (i) a one-way valve associated with the first end of the suction tube and permitting material to flow from the suction tube into the vacuum chamber but preventing material from flowing from the vacuum chamber into the suction tube.

2. The combination of claim 1 wherein the vacuum chamber has a length and a pair of opposite ends, wherein the first end of the suction tube is connected to a first one of the pair of opposite ends of the vacuum chamber and the two way conduit is connected to the vacuum chamber at the second one of the pair of opposite ends of the vacuum chamber.

3. The combination of claim 2 wherein the overpressure conduit interconnects the hand pump squeeze bulb with the vacuum chamber so as to enhance a flow of material from the vacuum chamber and into the collection bag through the one-way valve associated with the outlet end of the vacuum chamber.

4. The combination of claim 1 wherein first end of the suction tube is connected to communicate with the interior of the vacuum chamber through a connector permitting the suction tube to extend into the vacuum chamber an adjustable distance.

5. A combination including a multi-function hand pump and a collection bag, the combination comprising:
   (a) a multi-function hand pump including:
      (i) a resilient, hollow, elastic squeeze bulb having a pair of openings;
      (ii) a check valve associated with a first one of the pair of openings, arranged to allow flow of a fluid into the squeeze bulb and to prevent outward flow of fluid from the squeeze bulb;
      (iii) a check valve associated with a second one of the pair of openings, arranged to allow flow of a fluid out from the squeeze bulb and to prevent inward flow of fluid into the squeeze bulb;
      (iv) a connector associated with each one of the pair of openings, whereby the squeeze bulb can be connected to a selected fluid conduit to provide, selectively, reduced or increased fluid pressure within the selected fluid conduit;
   (b) a collection bag having an interior;
   (c) a Venturi eductor having a discharge port communicating with the interior of the collection bag, the multi-purpose hand pump being connected with the Venturi eductor so as to drive a flow of air through the Venturi eductor; and
   (d) a vent located in the collection bag and arranged to permit an exhaust flow of air from the collection bag while material drawn into the Venturi eductor is retained within the collection bag.

6. A combination including a collection bag for fluids and a vacuum system for collecting a quantity of a fluid, the combination comprising:
   (a) structure defining a vacuum chamber having an outlet opening and a one-way discharge valve at the outlet opening, the outlet opening being located and arranged to allow passage of material from the vacuum chamber into an interior of the collection bag;
   (b) a two-way first conduit communicating between the interior of the vacuum chamber and a connector arranged to be connected to a pump capable of providing a reduction of pressure;
   (c) a second, overpressure, conduit communicating between the interior of the vacuum chamber and a connector arranged to be connected with a pump capable of providing an increased pressure;
   (d) a suction tube having a first end connected with and communicating with the interior of the vacuum chamber and having a second end open so as to receive and conduct a flow of fluid into the vacuum chamber; and
   (e) a one-way valve associated with the first end of the suction tube and permitting material to flow from the suction tube into the vacuum chamber but preventing material from flowing from the vacuum chamber into the suction tube, and wherein the combination is for use with a pump capable of providing a reduction of pressure in the first conduit and a pump capable of providing an increased pressure in the second, overpressure, conduit.

* * * * *